(12) United States Patent
Grace et al.

(10) Patent No.: US 6,168,600 B1
(45) Date of Patent: Jan. 2, 2001

(54) ACETABULAR REAMER BACKING PLATE AND METHOD OF USE

(75) Inventors: Richard L. Grace, Russellville; Dan Duerr, Rsul; Jeff Grace, Dover, all of AR (US)

(73) Assignee: Grace Manufacturing, Inc., AR (US)

( * ) Notice: Under 35 U.S.C. 154(b), the term of this patent shall be extended for 0 days.

(21) Appl. No.: 09/378,085

(22) Filed: Aug. 20, 1999

(51) Int. Cl.$^7$ ................................................ A61B 17/00
(52) U.S. Cl. ............................ 606/81; 606/86; 623/22.21
(58) Field of Search .................................. 606/81, 80, 84, 606/173, 79, 172, 180, 86, 90, 91, 99; 623/22.21, 22.39, 22.31, 22.32; 408/14; 407/54, 61

(56) References Cited

U.S. PATENT DOCUMENTS

| | | | |
|---|---|---|---|
| 4,296,822 | * 10/1981 | Ormsbuy | 175/429 |
| 5,100,267 | 3/1992 | Salyer | 407/54 |
| 5,116,165 | 5/1992 | Salyer | 407/54 |
| 5,171,243 | * 12/1992 | Kashuba et al. | 606/86 |
| 5,302,234 | * 4/1994 | Grace et al. | 156/640 |
| 5,462,548 | * 10/1995 | Pappas et al. | 606/80 |
| 5,658,290 | * 8/1997 | Lechot | 606/80 |
| 5,709,688 | 1/1998 | Salyer | 606/81 |

* cited by examiner

Primary Examiner—Pedro Philogene
(74) Attorney, Agent, or Firm—Kevin M. Faulkner; Charles D. Gunter, Jr.

(57) ABSTRACT

The present invention is a backing plate for an acetabular reamer assembly that allows for the attachment of a reamer driver. The acetabular reamer assembly comprises a cutting cup and backing plate, the cutting cup having an external surface with cutting teeth formed therein and having an internal surface, the cutting cup terminating in a peripheral edge. The rigid backing plate has a planar surface which terminates in an outer circumferential edge, the outer circumferential edge being coupled to the peripheral bottom edge of the cutting cup, the rigid plate also having an internal edge profile. The internal edge profile of the rigid backing plate has at least two finger elements protruding from the outer circumferential edge thereof towards a central vertical axis drawn perpendicular to the planar surface of the plate. Further, the finger elements of the backing plate form a holding opening for a reamer driver. The internal edge profile of the backing plate forms at least one observation opening in addition to the holding opening to allow bone fragments forming within the acetabular reamer to be visually inspected while the reamer is in use. The finger elements terminate to form a contact surface to make firm contact with the driver when inserted in the holding opening. The contact surface can be simple or complex. Further, the internal edge profile is continuous so that the machining process for the backing plate is simplified.

28 Claims, 3 Drawing Sheets

ACETABULAR REAMER BACKING PLATE AND METHOD OF USE

BACKGROUND OF THE INVENTION

1. Field of the Invention

The present invention relates to acetabular reamer backing plates. In particular, the present invention relates to the design and use of backing plates for acetabular reamers that allow for the attachment of a driver and openings for allowing the surgeon to observe the bone cuttings within the cutting cup and make cleaning of the bone cuttings from the cup easier.

2. Description of the Prior Art

Acetabular reamers are surgical cutting tools used primarily to cut into bone for the implantation of joint prostheses. The most common use of an acetabular reamer is to replace the hip joint, wherein the greater trochanter of a femur and the acetabulum are replaced with a ball and socket-type of protheses, respectively. In order to perform such operations as to replace the hip joint, the surgeon must ream a portion of the bone and other tissue from the acetabulum to allow placement of the prosthetic socket. The reaming of the bone is accomplished by use of an acetabular reamer assembly.

The acetabular reamer assembly is composed of a cutting cup and a backing plate. A driver is then inserted into the backing plate to turn the cutting cup. The driver is in turn mounted in the chuck of a portable drill or flexible powered shaft. The tissue in the joint to be replaced is cut by rotating the cutting cup within the joint. A plurality of cutting edges are located along the outside surface of the cutting cup. Typically, the cutting edges extend through the cup and allow for cut tissue to fall and collect within the interior of the cup. Several prior art patents disclose methods of making acetabular cutting cups, including U.S. Pat. Nos. 5,709,688, 5,302,234, 5,116,165, and 5,100,267.

One problem with presently used acetabular reamers is the design of the backing plates. The backing plate is used to form the mechanical coupling between the reamer driver, which is typically a shaft that extends to an electric drill at one end and the cutting cup at the other. Once the plate is in place on the cutting cup and the driver is inserted into a hole in the plate, a closed cavity is typically formed wherein no spaces are left for bone and tissue fragments to escape. Thus, in most acetabular reamers, in order for the surgeon to judge the cutting progress and to remove excess tissue, the driver must be removed from the cutting tool, and often the backing itself. Removing the driver typically means that the surgeon must stop the procedure. This is a disadvantage in surgical procedures as it adds time and the possibility of imprecision.

At the same time, it is critical that the backing plate fit the driver snugly. This is important because acetabular reamers must be capable of producing cavities with very close tolerances. The cutting cups have precise dimensions and are light in weight and must fit on an appropriate tool driver with a minimum of free play and must be quick and easy to install and remove without tools. Although one backing plate has been shown in U.S. Pat. No. 5,709,688 to have small debris openings, these have the drawback of being relatively small and thus do not allow for easy removal of debris from within the cup interior. Further, this prior art backing plate has a number of independent openings, each requiring a separate starting hole in the machining process to form the backing plate. Thus, there is a need for a backing plate on an acetabular reamer cup with an opening or openings which allow greater physical and visual access to the interior of the cup while simplifying the machining operation in the manufacture of the plate. The present invention is directed towards such a need.

SUMMARY OF THE INVENTION

The present invention is an improvement in acetabular reamer assemblies, and in particular discloses an improved backing plate that allows for high tolerances in cutting, while also allowing the surgeon to visually inspect the bone fragments being cut, and to allow for easy removal of bone fragments without having to remove the driver.

The present invention is a backing plate for an acetabular reamer assembly that allows for the attachment of a reamer driver. The acetabular reamer assembly comprises a cutting cup and backing plate, the cutting cup having an external surface with cutting teeth formed therein and having an internal surface, the cutting cup terminating in a peripheral edge. The rigid backing plate has a planar surface which terminates in an outer circumferential edge, the outer circumferential edge being coupled to the peripheral bottom edge of the cutting cup, the rigid plate also having an internal edge profile. The internal edge profile of the rigid backing plate has at least two finger elements protruding from the outer circumferential edge thereof towards a central vertical axis drawn perpendicular to the planar surface of the plate. Further, the finger elements of the backing plate form a holding opening for a reamer driver.

The internal edge profile of the backing plate forms at least one observation opening in addition to the holding opening to allow bone fragments forming within the acetabular reamer to be visually inspected while the reamer is in use. The finger elements terminate to form a contact surface to make firm contact with the driver when inserted in the holding opening. The contact surface can be simple or complex. Further, the internal edge profile is continuous so that the machining process for the backing plate is simplified.

Thus, one object of the present invention is to provide a backing plate that allows the medical practitioner more control in reaming bone and other tissue from a patient's joint.

Another object of the present invention is to provide the medical practitioner an improved observation opening for visually inspecting the progress of the reaming procedure.

Yet another object of the present invention is to provide a backing plate that can be machined in fewer steps, thus simplifying the machining of the backing plate and making it less expensive.

Yet another object of the present invention is to provide a backing plate that allows for easy removal of bone fragments within the cavity of the cutting cup.

Yet another object of the present invention is to provide a backing plate that reduces the compaction of bone fragments and other tissues within the cavity formed by the reamer cup and backing plate, thus improving the cutting ability of the cutting edges of the cup.

The features and elements of the present invention will accomplish these objects. Additional objects, features and advantages will be apparent in the written description which follows.

DETAILED DESCRIPTION OF THE INVENTION

Figure 1:
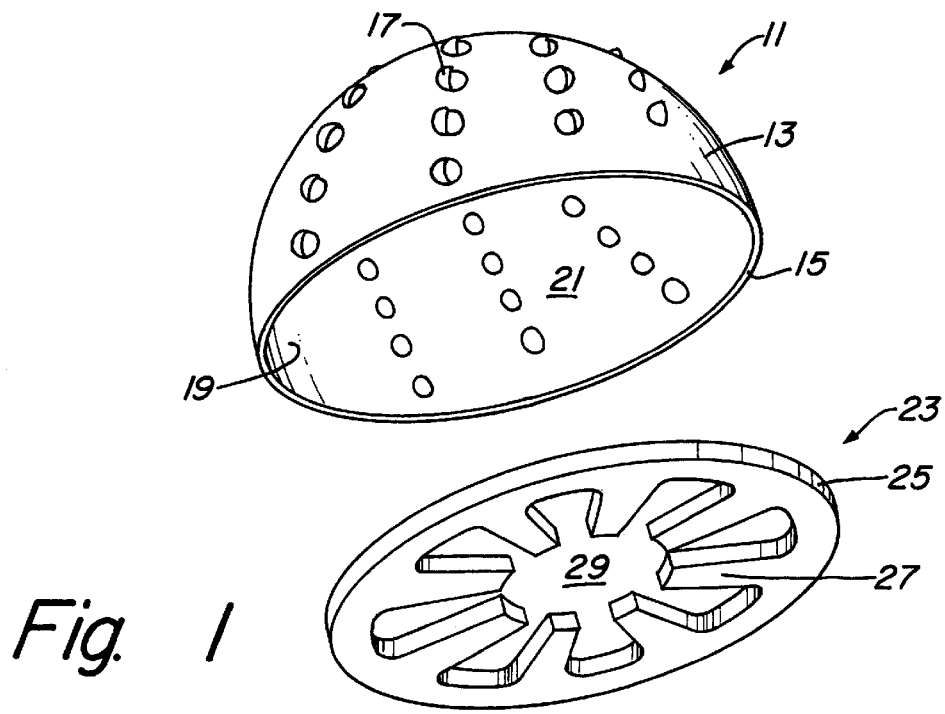
FIG. 1 is a perspective view of an acetabular reamer assembly.
Figure 2:
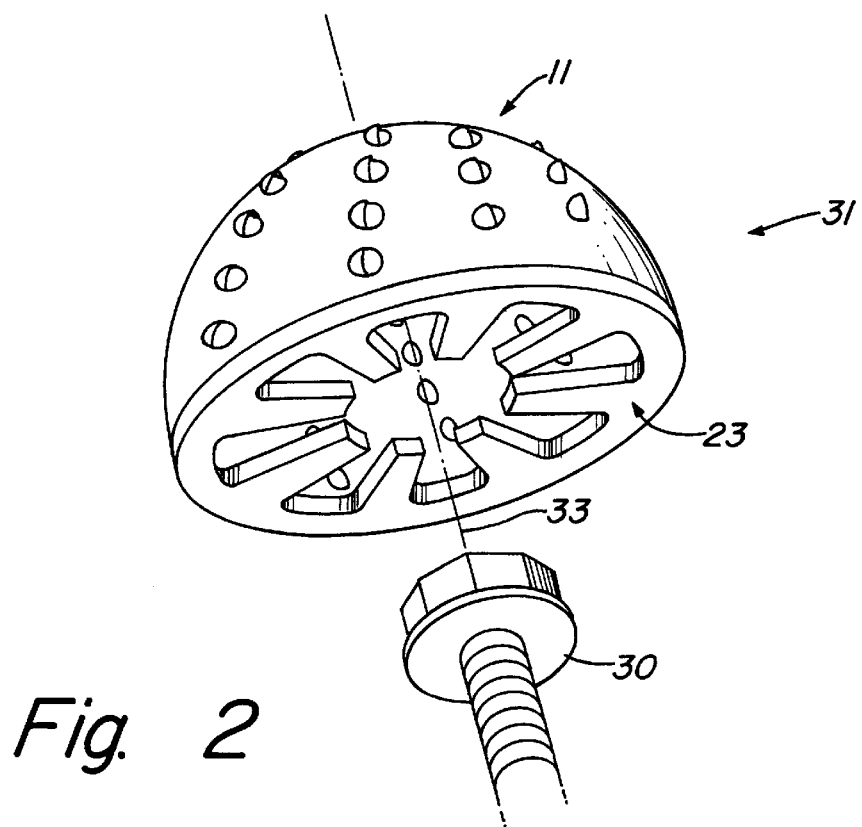
FIG. 2 is a perspective view of the cutting cup and backing plate with a reamer driver.

Referring to FIGS. 1 and 2, the acetabular reamer assembly consists of a cutting cup 11 and backing plate 23. The reamer driver 30 is inserted into the assembled reamer assembly as shown in FIG. 2. The cutting cup 11 comprises an external surface 13 and an internal surface 19, the internal surface forming cavity 21. The cutting cup 11 can be in various sizes depending on the size of the patient and the joint to be reamed. Further, the cutting cup 11 can be in various shapes, although a hemispherical shape as depicted in FIGS. 1 and 2 is most common, as this shape is complementary to the shape of a normal socket joint in a human.

Extending from the internal surface 19 to the external surface 13 are a plurality of cutting edges 17. Typically, these edges can be arranged in a concentric configuration, the cutting edges 17 each facing in the same direction. There are various methods of making these cutting edges such as that disclosed in U.S. Pat. No. 5,302,234, herein incorporated by reference.

The cutting cup 11 has a peripheral edge 15. In the embodiment shown in FIG. 1, the peripheral edge 15 is relatively uniform. In other embodiments, the edge can have notches or protrusions for fastening the backing plate 23. The backing plate has a complementary outer circumferential edge 25 that fits within the peripheral edge 15 of the cutting cup 11. It is understood by those skilled in the art that if there are notches or protrusions in the peripheral edge 15, the backing plate 23 will have complementary elements. FIG. 2 shows the backing plate 23 attached to the cutting cup 11. Each of the backing plates of the invention described infra are attached to a corresponding cutting cup by such means as traditional welding, laser welding, or by mechanically locking the two parts together, or by other fastening means known to those skilled in the art.

The backing plate 23 is a rigid plate, typically milled from a plate of stainless steel or other rigid alloy or plastic material appropriate for surgical procedures. The backing plate 23 has a planar surface defined by a front face and a back face, described in more detail infra. The backing plate 23 also has a continuous internal profile forming finger elements 27, the internal profile also described in more detail infra. The internal profile forms a holding opening 29 wherein the reamer driver 30 can be inserted and held. Typically, the driver 30 has a shape that is complementary to the internal profile (24 in FIG. 3, 44 in FIG. 4, and 64 in FIG. 5). Thus, if there are, for example, 6 finger elements 27 in the backing plate, then the appropriate driver will have a hexagonal shaped end. This allows for a tight fit between the driver 30 and backing plate 23, which in turn gives the medical practitioner greater control of the acetabular reamer assembly during an operation or medical procedure. The cutting cup 11 and holding opening 29 form a vertical axis 33 drawn perpendicular to the planar surface of the backing plate 23, the vertical axis located at the center of the holding opening 29.

Figure 3A:
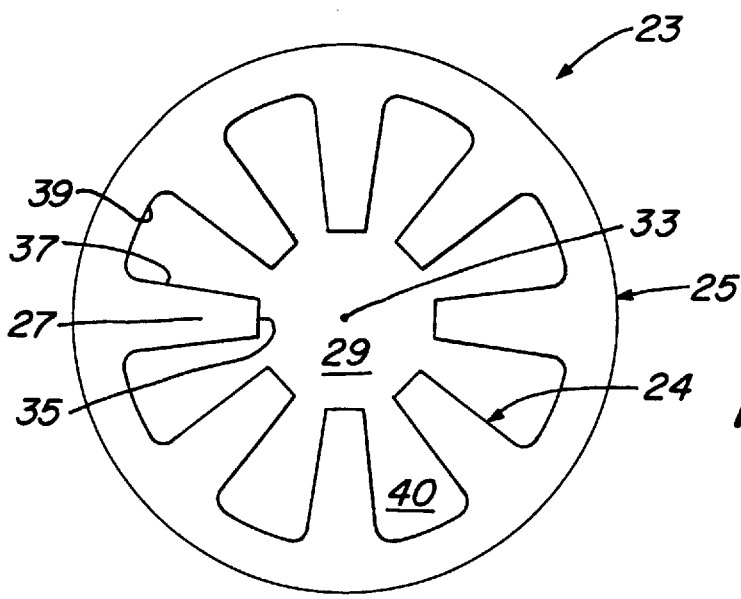
FIG. 3A is a top view of one embodiment of the backing plate of the invention.
Figure 3B:
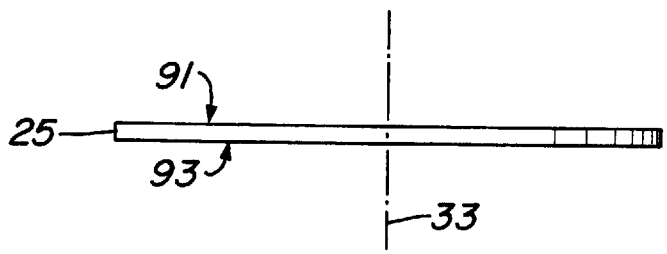
FIG. 3B is a side view of the backing plate in FIG. 3A.

Referring now to FIGS. 3A and 3B, one embodiment of the backing plate of the invention is described in greater detail. Backing plate 23 has a planar top surface 91 and a planar bottom surface 93, each planar surface terminating in outer circumferential edge 25. The backing plate 23 also has an internal edge profile 24, wherein the internal edge profile 24 forms at least one observation opening 40 in addition to the holding opening 29. The observation openings 40 are formed by the space between the finger elements 27, the embodiment in FIG. 3A having 8 finger elements.

Each finger element has a protruding edge 37, and a contact surface 35. The internal profile between finger elements is defined by spacing edge 39. The finger elements of the present invention protrude away from the circumferential edge, the protruding edge defining the length of protrusion away from the circumferential edge and the spacing edge. The finger elements 27 typically form a uniform configuration such that the internal profile 24 has a common repeating pattern of contact surfaces. Further, the contact surfaces 35 also form a symmetric holding opening 29 to allow the insertion of a reamer driver 30. The at least two finger elements 27 each terminate in a contact surface 35 that makes firm contact with an associated driver to hold the driver within the holding opening, perpendicular to the top and bottom planar surfaces 91 and 93.

Figure 4:
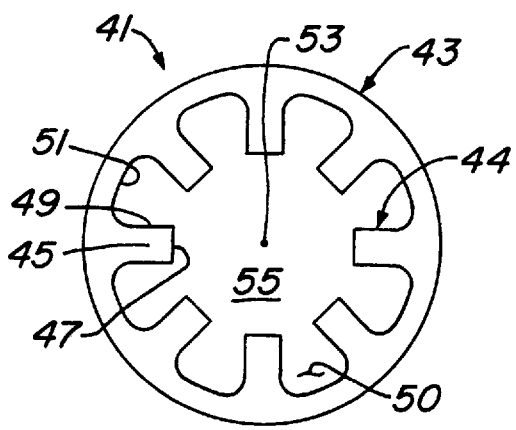
FIG. 4 is a top view of another embodiment of the backing plate of the invention.

The backing plate of the acetabular reamer assembly can take on various shapes and sizes as shown in FIGS. 4 though 7. Specifically, referring to FIG. 4 is a backing plate 41 similar in shape to the backing plate 23, but smaller in size due to the smaller circumference of outer circumferential edge 43 relative to outer circumferential edge 25. The backing plate 41 has an outer circumferential edge 43 and an internal edge profile 44. The backing plate 43 also has at least two finger elements 45, each element having a protruding edge 49 and a contact surface 47, the contact surfaces of the at least two finger elements 45 being symmetric about the vertical axis 53 of backing plate 41. Further, holding opening 55 is defined by the continuous internal edge profile 44, the holding opening 55 being symmetric about the vertical axis 53. The internal profile between the finger elements is defined by spacing edge 51.

The internal edge profile 44 forms at least one observation opening 50, the openings typically located between each finger element 45. Each embodiment of the backing plate of the present invention has a number of observation openings defined by the shape of the internal edge profile. The observation openings 50 in backing plate 41, and observation openings 40 in backing plate 23, allow the medical practitioner to observe the cavity 21 of the cutting cup 11 when the driver 30 is inserted in, for example, holding openings 29 and 55. Thus, as the cutting edges 17 cut bone and other tissue, the tissue collects within cavity 21. The medical practitioner is able to view the cuttings within the cavity 21 to determine how much cutting of the bone has occurred, and when and if the cutting cup 11 needs to be emptied of tissue cuttings. Further, the observation openings 40 and 50 allow the medical practitioner to more easily clean tissue fragments and cuttings from the cavity 21.

Since drivers are typically of the same diameter, it is often desirable to make the size of the holding opening from one backing plate to the other the same. Thus, while different drivers have different outer circumferences defined by their outer circumferential edges, each has a similarly sized holding opening. For example, plate 23 in FIG. 3A has a larger circumference than plate 43 in FIG. 4, yet both have the same size holding opening 29 and 55, respectively. It is the difference in the length of the finger elements that creates this effect. The size of the holding opening is largely dependent upon the length of the protruding edges, protruding edge 37 being greater in length than protruding edge 49. However, it is to be understood that the length or shape of the finger elements can be varied to fit any size driver.

Figure 5:
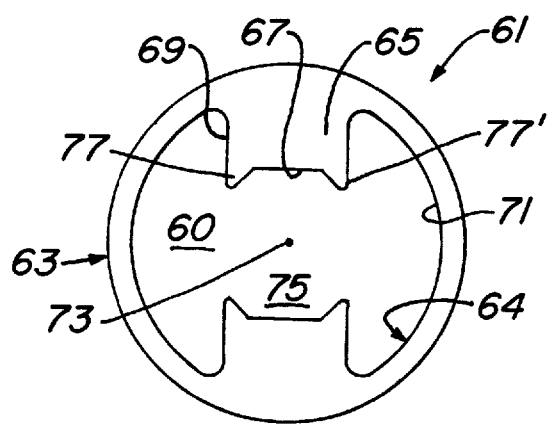
FIG. 5 is a top view of another embodiment of the backing plate of the invention.

The backing plate can also have more complex finger element formations. FIG. 5 shows another embodiment of the invention, wherein a more complex plate is depicted. Backing plate 61 has an outer circumferential edge 63 and an internal edge 64. The internal profile between the finger elements is defined by spacing edge 71. Backing plate 61 also has two finger elements 65 that protrude from edge 71 to form protruding edge 69, terminating in contact surface 67. Thus, the two finger elements are in direct opposition, protruding towards the central vertical axis 73.

The contact surface 67 can have a complex profile, as shown in FIG. 5, wherein the contact surface 67 has bevel edges 77 and 77'. The complex contact surface 67 with bevel edges 77 and 77' creates a holding opening 75 that is symmetric about central vertical axis 73, and allows for firm contact with a driver, the reamer driver 30 and contact surface 67 making greater surface-to-surface contact, thus creating a tight fit and better control for the medical practitioner. Also, the at least one observation opening 60 is larger in the configuration of backing plate 61 relative to other configurations with a greater number of finger elements.

Figure 6:
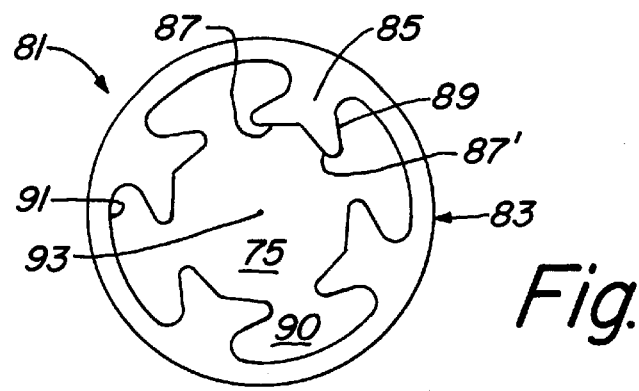
FIG. 6 is a top view of another embodiment of the backing plate of the invention

Yet another embodiment of the backing plate of the invention is described with reference to FIG. 6. The backing plate 81 has a circumference defined by outer circumferential edge 83. The backing plate 81 has finger elements 85 defined by protruding edges 89 and contact surfaces 87 and 87'. The edges 89, 87, 87' and the internal profile between the finger elements defined by spacing edge 91 make up the internal edge profile 84. Between each of the finger elements 85 is an observation opening 90. A holding opening 95 is centered around a vertical axis 93. The holding opening 95 in backing plate 81 is octagonal in shape, thus fitting a comparably shaped octagonal driver head.

Figure 7:
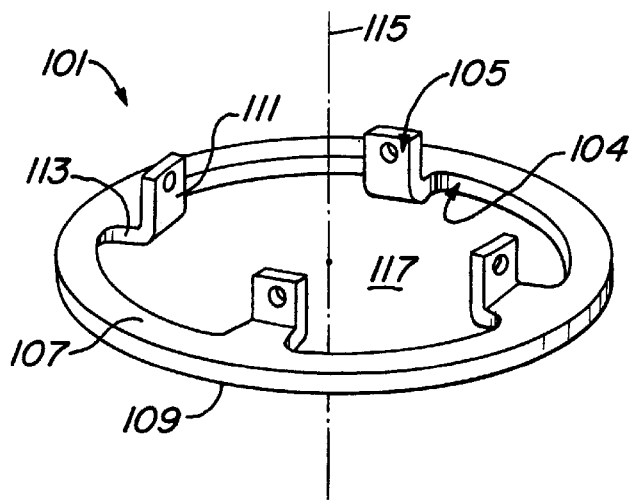
FIG. 7 is a perspective view of another embodiment of the backing plate of the invention.

Yet another embodiment of the backing plate of the invention is described with reference to FIG. 7. The various elements and edges of this embodiment are similar to those discussed in the previous embodiments, with the added feature of having finger elements that are bent from a plane perpendicular to the vertical axis, thus forming larger contact surfaces. Backing plate 101 has internal edge profile 104 and finger elements 105. The backing plate has a top surface 107 and a bottom surface 109, each substantially perpendicular to the vertical axis 115.

In backing plate 101, each finger element is bent at 113 to form contact surface 111. The contact surface 111 is substantially parallel to the vertical axis 115, thus making flush contact with a driver head once inserted into the holding opening 117.

Figure 8:
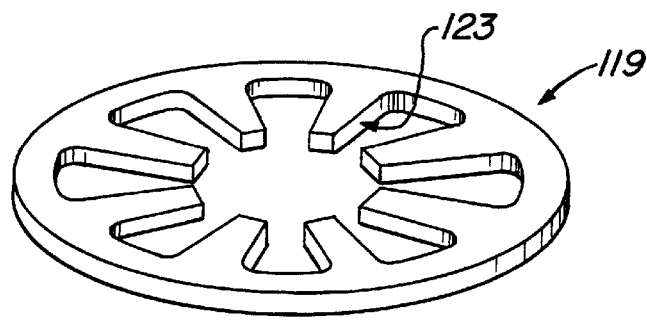
FIG. 8 is a perspective view of the backing plate and cut-out from the manufacturing procedure.

In manufacturing the backing plates 23, 41, 61, 81, 101, or other backing plates of the invention, a substantially flat plate made from a rigid material is cut to fit the desired outer circumferential edge, followed by cutting out the internal edge profile. This is shown in FIG. 8, wherein cut-out 121 is removed to form backing plate 119. Since the internal edge profile 123 is continuous in the backing plate of the invention (and also, for example, 24 in backing plate 23, 44 in backing plate 41, and 64 in backing plate 61), the method of cutting out the shapes of the finger elements requires only one starting hole, a starting hole being required for most machining procedures wherein a cut is desired within a structure.

Once the backing plate is fastened to the cutting cup, the reamer driver can be inserted into the holding opening, the contact surface of the at least two finger elements making firm contact with the driver. The driver may also have a chuck that allows for the medical practitioner to apply pressure along the central vertical axis, the driver being substantially parallel with the vertical axis of the backing plate. The driver is then coupled at the other end to an electrical or air powered device such as a drill to turn the driver, and hence the cutting cup, at a controlled rate of rotation. Once force is applied to the driver by the medical practitioner against the surface to be cut in the patient, bone or other tissue fragments collect in the cavity of the cutting cup.

The acetabular reamer assembly is used in bone reaming operations in the following manner. First, depending on the size of the patient, and the joint to be reamed, the cutting cup 11 is first chosen by the medical practitioner. The complementary backing plate is typically pre-fastened to the cutting cup as described supra (see FIG. 2) prior to being received by the end user, such as a surgeon. However, for cutting cups of the same or similar size, there may be a choice as to the desired shape and size of the backing plate. The acetabular reamer cutting cup having a backing plate is chosen to have a holding opening that is complementary to the particular reamer driver used by the surgeon. For example, if the driver has a hexagonal shape, the acetabular reamer cutting cup having the backing plate should be chosen such that the holding opening corresponds to the driver to be used.

As bone is being reamed from the socket, fragments of bone and tissue collect within cavity 21. Due to the presence of the observation openings in the backing plate of the present invention, less packing occurs when compared to prior art backing plates. Also, the user can view her progress as the bone is cut away, making the reaming procedure more efficient and precise.

Thus, there are several advantages to the backing plate of the present invention. The open finger design provides a backing plate with observation openings so that the medical practitioner can view the cavity within the cutting cup.

Another advantage is that the finger elements allow for variation in the finger width, length, and number of finger elements over the entire range of sizes required to achieve maximum visibility for the medical practitioner.

Another advantage in the finger element design is that it allows for a multiplicity of driver shapes to be employed with the backing plate.

Another advantage is in the manufacturing of the backing plate which allows for a reduced number of starting holes required in most numerically controlled machining processes such as plasma cutting, wire EDM or laser cutting.

Yet another advantage of the present invention is the ease with which bone cuttings can be removed from the interior of the cutting cup either during the cutting procedure, or after the cutting procedure, as the bone cuttings and other tissue is often used in subsequent medical procedures on the same or other patient.

Yet another advantage of the present invention is the reduction of bone fragment packing within the cutting cup, thus making it easier for bone fragments and other material to escape from within the cup and thus increasing the efficiency of the bone cutting.

While the invention has been shown in only one of its forms, it is not thus limited but is susceptible to various changes and modifications without departing from the spirit thereof.

What is claimed is:

1. An acetabular reamer assembly allowing for the attachment of a reamer driver, the acetabular reamer assembly comprising:
    a cutting cup having an external surface with cutting teeth formed therein and having an internal surface, the cutting cup terminating in a peripheral edge;
    a rigid backing plate having a planar surface which terminates in an outer circumferential edge, the outer circumferential edge being coupled to the peripheral edge of the cutting cup, the rigid plate also having an internal edge profile;
    wherein the internal edge profile has at least two finger elements protruding from the outer circumferential edge thereof towards a central vertical axis drawn perpendicular to the planar surface of the plate; and
    wherein the finger elements form a holding opening for a reamer driver.

2. The acetabular reamer assembly of claim 1, wherein the internal edge profile of the backing plate forms at least one observation opening in addition to the holding opening to allow bone fragments forming within the acetabular reamer to be visually inspected while the reamer is in use.

3. The acetabular reamer assembly of claim 1, wherein a plurality of observation openings are formed by the finger elements in addition to the holding opening.

4. The acetabular reamer assembly of claim 1, wherein the at least two finger elements each terminate in a contact surface that makes firm contact with an associated driver to hold the driver within the holding opening, perpendicular to the backing plate planar surface.

5. The acetabular reamer assembly of claim 4, wherein the contact surface of the at least two finger elements has a complex profile to grip the driver.

6. The acetabular reamer assembly of claim 5, wherein the complex profile forms a hexagonal shaped holding opening.

7. The acetabular reamer assembly of claim 5, wherein the complex profile forms a round shaped holding opening.

8. The acetabular reamer assembly of claim 5, wherein the complex profile forms a square shaped holding opening.

9. The acetabular reamer assembly of claim 5, wherein the complex profile forms an octagonally shaped holding opening.

10. The acetabular reamer assembly of claim 5, wherein the complex profile forms a series of polygon shaped openings arranged symmetrically about the central vertical axis of the rigid plate.

11. The acetabular reamer assembly of claim 4, wherein two finger elements in direct opposition protrude towards the central vertical axis.

12. The acetabular reamer assembly of claim 11, wherein the contact surface of the two finger elements are shaped to grip a hexagonally shaped driver fully on two sides, and at least partially on four sides of the hexagonally shaped driver.

13. The acetabular reamer assembly of claim 1, wherein the internal edge profile is continuous, thus allowing for a single starting hole in the machining operation of the backing plate.

14. The acetabular reamer assembly of claim 1, wherein there is only one continuous internal edge profile.

15. A method of using an acetabular reamer assembly in a bone reaming operation, the method comprising the steps of:
    providing a cutting cup having an external surface with cutting teeth formed therein and having an internal surface, the cutting cup terminating in a peripheral edge;
    providing a rigid backing plate having a planar surface which terminates in an outer circumferential edge, the outer circumferential edge being coupled to the peripheral edge of the cutting cup, the rigid plate also having an internal edge profile;
    the internal edge profile having at least two finger elements protruding from the outer circumferential edge thereof towards a central vertical axis drawn perpendicular to the planar surface of the plate, thereby forming a holding opening for a reamer driver;
    wherein the internal edge profile of the rigid plate forms at least one observation opening in addition to the holding opening;
    a reamer driver into the holding opening;
    driving the rotating acetabular reamer cutting cup into a bone surface, thus cutting fragments of bone tissue; and
    using the observation opening in the rigid plate to visually inspect bone fragments forming within the acetabular reamer while the reamer is in use.

16. The method of claim 15, wherein the internal edge profile of the backing plate forms at least one observation opening in addition to the holding opening to allow bone fragments forming within the acetabular reamer to be visually inspected while the reamer is in use.

17. The method of claim 15, wherein a plurality of observation openings are formed by the finger elements in addition to the holding opening.

18. The method of claim 15, wherein the at least two finger elements each terminate in a contact surface that makes firm contact with an associated driver to hold the driver within the holding opening, perpendicular to the backing plate planar surface.

19. The method of claim 18, wherein the contact surface of the at least two finger elements has a complex profile to grip the driver.

20. The method of claim 19, wherein the complex profile forms a hexagonal shaped holding opening.

21. The method of claim 19, wherein the complex profile forms a round shaped holding opening.

22. The method of claim 19, wherein the complex profile forms a square shaped holding opening.

23. The method of claim 19, wherein the complex profile forms an octagonally shaped holding opening.

24. The method of claim 19, wherein the complex profile forms a series of polygon shaped openings arranged symmetrically about the central vertical axis of the rigid plate.

25. The method of claim 18, wherein two finger elements in direct opposition protrude towards the central vertical axis.

26. The method of claim 25, wherein the contact surface of the two finger elements are shaped to grip a hexagonally shaped driver fully on two sides, and at least partially on four sides of the hexagonally shaped driver.

27. The method of claim 15, wherein the internal edge profile is continuous, thus allowing for a single starting hole in the machining operation of the backing plate.

28. The method of claim 15, wherein there is only one continuous internal edge profile.

* * * * *